(12) United States Patent
Becq et al.

(10) Patent No.: US 7,605,153 B2
(45) Date of Patent: Oct. 20, 2009

(54) USE OF PAULLONE DERIVATIVES FOR THE PRODUCTION OF MEDICAMENTS FOR THE TREATMENT OF MUCOVISCIDOSIS AND DISEASES RELATED TO PROTEIN ADDRESSING ERRORS IN CELLS

(75) Inventors: Frédéric Becq, Poitiers (FR); Laurent Meijer, Roscoff (FR); Conrad Kunick, Hamburg (DE)

(73) Assignees: Centre National de la Recherche Scientifique - CNRS, Paris Cedex (FR); Universitè de Poitiers, Poitiers, Cedex (FR)

( * ) Notice: Subject to any disclaimer, the term of this patent is extended or adjusted under 35 U.S.C. 154(b) by 0 days.

(21) Appl. No.: 11/786,784

(22) Filed: Apr. 12, 2007

(65) Prior Publication Data

US 2008/0076756 A1    Mar. 27, 2008

Related U.S. Application Data

(63) Continuation of application No. PCT/FR2005/002556, filed on Oct. 14, 2005.

(51) Int. Cl.
*A61K 31/55* (2006.01)
*A61P 11/00* (2006.01)

(52) U.S. Cl. ..................................... 514/215
(58) Field of Classification Search ............ None
See application file for complete search history.

(56) References Cited

U.S. PATENT DOCUMENTS

| | | | |
|---|---|---|---|
| 6,448,264 B2 * | 9/2002 | Misra | 514/303 |
| 6,555,539 B2 * | 4/2003 | Reich et al. | 514/252.02 |
| 7,038,045 B2 * | 5/2006 | Guzi et al. | 544/194 |
| 7,196,090 B2 * | 3/2007 | Connolly et al. | 514/234.5 |
| 7,196,104 B2 * | 3/2007 | Askew et al. | 514/342 |
| 7,232,814 B2 * | 6/2007 | Meijer et al. | 514/212.06 |
| 7,268,136 B2 * | 9/2007 | Green et al. | 514/248 |
| 2003/0181439 A1 | 9/2003 | Meijer et al. | |
| 2007/0275986 A1 | 11/2007 | Becq et al. | |

FOREIGN PATENT DOCUMENTS

| WO | WO 00/24391 | | 5/2000 |
|---|---|---|---|
| WO | WO 0160374 A1 * | | 8/2001 |

OTHER PUBLICATIONS

Becq, et al., "Development of Substituted Benzo[c]quinolizinium Compounds as Novel Activators of the Cystic Fibrosis Chloride Channel", The Journal of Biological Chemistry, vol. 274, No. 39, Sep. 24, pp. 27415-27425, (1999).

Dormer, et al., "Correction of delF508-CFTR activity with benzo(c)quinolizinium compounds through facilitation of its processing in cystic fibrosis airway cells", Journal of Cell Science, 114 (22), pp. 4073-4081, (2001).

* cited by examiner

*Primary Examiner*—Brian-Yong S Kwon
(74) *Attorney, Agent, or Firm*—Harness, Dickey & Pierce, P.L.C.

(57) ABSTRACT

The invention relates to paullone derivatives for the production of medicaments for the treatment of mucoviscidosis and diseases related to protein addressing errors in cells, said derivatives being of general formula (1): wherein X=C=O, C—S—CH$_3$, C—S, —C—NHOH, Z—C or N, Y— with the adjacent ring, a phenyl or thienyl group, the ring(s) of said derivatives being optionally substituted with one or more halogen atoms, hydroxy, alkylenehydroxy, alkynealkylenehydroxy, alkynehydroxycyclohexyl, alkyl, alkoxy, alkylenealkoxy, or alkylenecyano groups where the alkylene group is either saturated or unsaturated, the groups having a straight or branched chain with C1 to C18, said chain being optionally substituted with one or more hydroxy or amino groups, or one or more trifluoromethyl, —COM, —COOM, or —CH$_2$COOM groups (where M=H, C1 to C18 straight or branched chain alkyl, optionally substituted with one or more hydroxy and/or amino groups) nitroso, or cyano, $R^5$=H, or C1 to C5 alkyl and $R^{12}$=H, or —C—CO$_2$—(CH$_3$)$_3$ and the physiologically-acceptable salts and derivatives thereof.

15 Claims, 5 Drawing Sheets
(1 of 5 Drawing Sheet(s) Filed in Color)

kenpaullone        alsterpaullone

A. Cos7/GFP/CFTR-DF508

B. Cos7/GFP/CFTR-DF508
+ kenpaullone 100µM 2h

USE OF PAULLONE DERIVATIVES FOR THE PRODUCTION OF MEDICAMENTS FOR THE TREATMENT OF MUCOVISCIDOSIS AND DISEASES RELATED TO PROTEIN ADDRESSING ERRORS IN CELLS

CROSS-REFERENCE TO RELATED APPLICATIONS

This application is a continuation of PCT/FR2005/002556, filed Oct. 14, 2005, which claims priority to French Application No. 04/10961, filed Oct. 15, 2004. Both of these applications are incorporated by reference herein.

BACKGROUND

The invention aims at using kenpaullone and kenpaullone derivatives for the production of medicaments able to restore addressing of proteins from the endoplasmic reticulum to the plasma membrane. It aims in particular at treating mucoviscidosis.

Mucoviscidosis (CF: Cystic fibrosis) is the most common recessive autosomal lethal genetic disease in European and North American populations. The CF gene (locus 7q31) encodes the protein called Mucoviscidosis Transmembrane Conductance Regulator (CFTR). Mutations of the CF gene cause abnormal transport of water and electrolytes through the cell membrane of various organs such as the lungs, sweat glands, the intestine and the exocrine pancreas. Although there are over 1,000 mutations of the CFTR protein, the most common mutation (70% of patients) is the deletion of a phenylalanine in the $NBF_1$ domain at position 508 (delF508). The main cause of mortality in CF patients is linked to this deletion and leads to infections or pulmonary insufficiency due to an increase in mucus viscosity. Such viscosity causes occlusion of respiratory airways and promotes infections by opportunistic bacteria. Furthermore, an aggravation is observed at the level of the digestive apparatus and the pancreas particularly (patient with pancreatic insufficiency). The CFTR protein is a glycoprotein of 1,480 amino acids, belonging to the ABC superfamily of membrane transporters. CFTR is a chloride ion channel localised in the apical plasma membrane of lung epithelial cells in healthy individuals. CFTR is responsible for trans-epithelial transport of water and electrolytes, thereby allowing hydration of lung airways in healthy individuals.

In CF patients homozygous for delF508 mutation, and more generally for class-II (mutations producing a protein that is absent from the cell membrane), this protein is absent from the plasma membrane due to faulty addressing of this protein, which remains in the endoplasmic reticulum (ER). In such cases, hydration of lung airways is no longer functional. The delF508 deletion alters the folding of the NBF1 domain and prevents the full maturation of the protein, which is therefore degraded very early during biosynthesis. However, if the delF508 protein is able to reach the membrane, it works as a chloride ion channel.

One of the keys to treating this disease therefore consists in re-addressing delF508 to the plasma membrane of the cells, where the transport activity of delF508 can be stimulated by physiological agonists.

SUMMARY

Surprisingly, in accordance with the present teachings, the inventors have found that paullone derivatives, known in particular for their anti-proliferative effect, are further capable of activating wild-type and mutated forms of CFTR, and inducing the relocation of delF508-CFTR protein to the plasma membrane, thereby restoring its trans-membrane transport capacity. Generally speaking, such derivatives can restore a protein addressing error in cells. Furthermore, these compounds have the advantage of being highly innocuous. In various aspects, the invention provides a new use of these derivatives in order to produce medicaments for the treatment of mucoviscidosis and other diseases linked to a protein addressing error in cells.

These derivatives are represented by general formula (I):

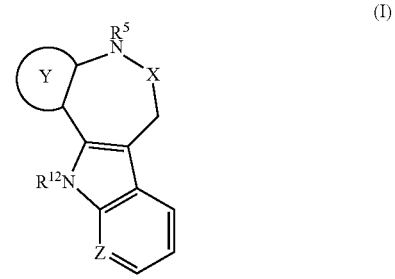

Where
X represents a C=O, C—S—$CH_3$, C—S or —C—NHOH group;
Z represents C or N;
Y represents a phenyl or a thienyl residue, together with the adjacent ring;

the ring(s) that constitute such derivatives being substituted as the case may be with one or more halogen atoms, hydroxyl, alkylenehydroxyl, alkynalkylenehydroxyl, alkynhydroxycyclohexyl, alkyl, alkoxyl, alkylenealkoxyl, alkylenecyano groups, the alkylene group being saturated or unsaturated, such C1 to C18 radicals having a straight or branched chain, the said chain being as the case may be substituted with one or more hydroxyl or amino groups, one or more trifluoromethyl groups, —COM, —COOM, or —$CH_2$COOM group (where M represents a hydrogen atom or a C1 to C18 alkyl group with a straight or branched chain substituted as the case may be with one or more hydroxyl and/or amino groups), a nitroso or a cyano group;
$R^5$ represents a hydrogen atom or a C1 to C5 alkyl group
$R^{12}$ represents a hydrogen atom or a —C—$CO_2$—$(CH_3)_3$ group, and the physiologically acceptable salts of these derivatives.

In a family of paullone derivatives, Y represents a phenyl residue, together with the adjacent ring, and Z=C. This family is represented by general formula (II):

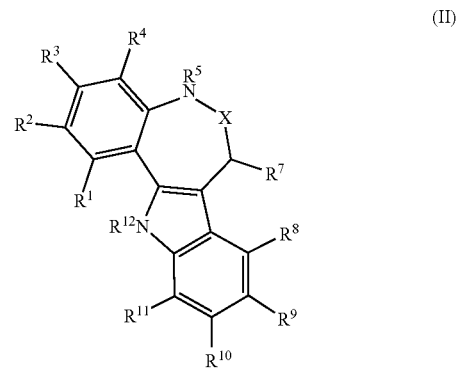

Where

X, $R^5$ and $R^{12}$ are as defined supra and $R^1$ to $R^4$, $R^7$ to $R^{11}$, identical or different, represent an atom of hydrogen, halogen (F, Cl, Br, I), a hydroxyl, alkylenehydroxyl, alkynalkylenehydroxyl, alkynhydroxycyclohexyl, alkyl, alkoxy, alkylenealkoxy, alkylenecyano group, these radicals having C1 to C18 straight or branched chains, the alkylene group being saturated or unsaturated; the said chain being as the case may be substituted with one or more hydroxyl or amino groups, a trifluoromethyl group, a —COM, —COOM or —CH$_2$COOM group (where M represents a hydrogen atom, a C1 to C18 alkyl group with a straight or branched chain, substituted as the case may be with one or more hydroxyl and/or amino groups), a nitroso group or a cyano group; and the physiologically acceptable salts of such derivatives.

In another family of paullones derivatives, Y represents a thienyl residue, together with the adjacent ring, and Z=C. This family is represented by general formula (III):

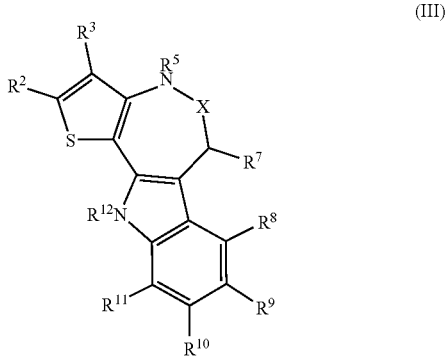

(III)

where the substituted groups have the meaning given supra with respect to formula (II).

In yet another family, Y forms a phenyl group together with the adjacent ring and Z=N. This family is represented by formula (IV):

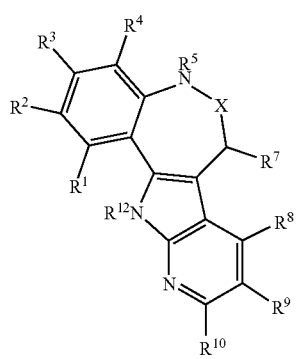

(IV)

where the substituted groups have the meaning given supra with respect to formula (II). In a group of paullone derivatives of these various families, X represents C=O.

The invention more specifically aims at a novel use of kenpaullone for treatment of mucoviscidosis or other diseases associated with protein addressing errors. The production of medicaments containing kenpaullone for treating such conditions is also provided. The kenpaullone used according to the invention is represented by formula (V):

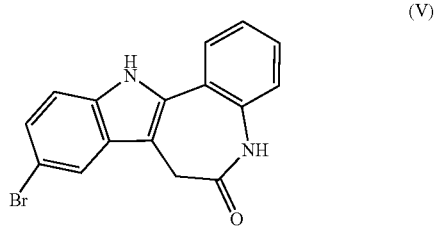

(V)

As the examples illustrate, kenpaullone is particularly efficient for inducing the membrane relocalization of the delF508-CFTR protein in mucoviscidosis, in which this protein is retained in the endoplasmic reticulum, and thus restoring its trans-membrane transport capacity.

When developing medicaments, the active principles used in therapeutically efficient quantities are mixed with pharmaceutically acceptable vehicles for the administration route chosen. Thus, for oral administration, medicaments are prepared in the form of gelatine capsules, tablets, SC tablets, capsules, pills, drops, syrups and similar. Such medicaments may contain 1 to 100 mg of active principle per unit. For parenteral administration (intravenous, subcutaneous, intramuscular injection), the medicaments are presented in the form of sterile or sterilisable solutions. They may also be in the form of suspensions or emulsions. The medicaments of the invention are more particularly administered in the form of aerosols.

Doses per administration unit may vary from 1 to 50 mg of active principle. The daily posology (e.g., dosage related to a therapeutically effective amount) is chosen so as to obtain a final concentration not exceeding 100 µM of paullone derivative in the blood of patients under treatment. Other characteristics and advantages of the invention will be described in the results reported below in order to illustrate the invention.

BRIEF DESCRIPTION OF THE DRAWINGS

In these examples, reference is made to FIGS. 1 to 5, which represent respectively.

Figure 1:
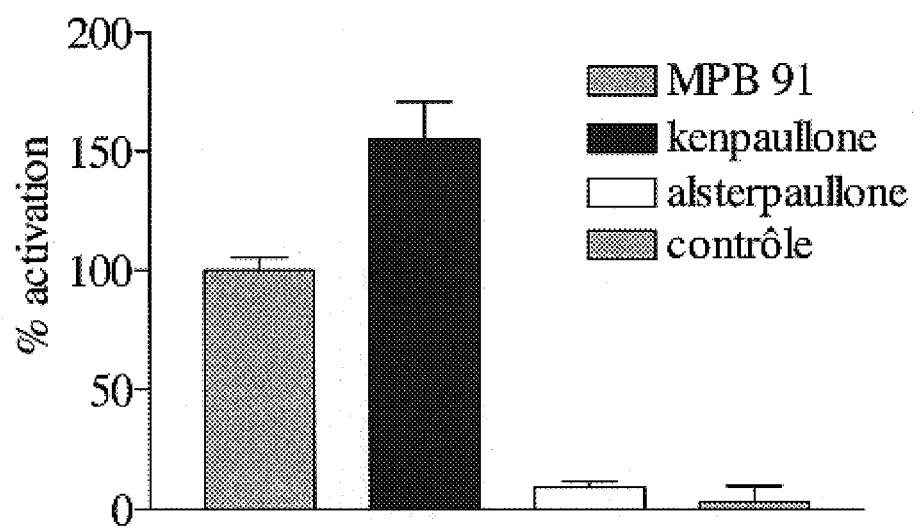
FIG. 1: a histogram showing the percentage of CFTR activation after treatment of CF15 cells under different conditions.
Figure 1:
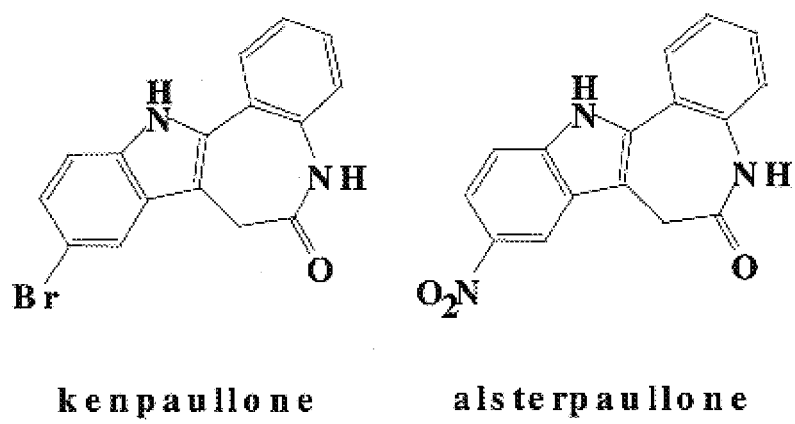

The patent or application file contains at least one drawing executed in color. Copies of this patent or patent application publication with color drawing(s) will be provided by the Office upon request and payment of the necessary fee.

DETAILED DESCRIPTION

In various aspects, the present disclosure provides a method of treating diseases linked to a protein addressing error in cells, such as mucoviscidosis (e.g., cystic fibrosis). In certain aspects, the active agents are paullone derivatives represented by the formula (I) comprising:

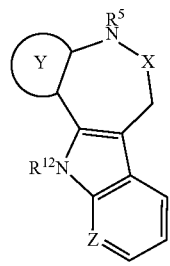
(I)

Where

X represents a C=O, C—S—CH$_3$, C—S or —C—NHOH group;

Z represents C or N;

Y represents a phenyl or a thienyl residue, together with the adjacent ring;

the ring(s) that constitute such derivatives being substituted as the case may be with one or more halogen atoms, hydroxyl, alkylenehydroxyl, alkynalkylenehydroxyl, alkynhydroxycyclohexyl, alkyl, alkoxyl, alkylenealkoxy, alkylenecyano groups, the alkylene group being saturated or unsaturated, such C1 to C18 radicals having a straight or branched chain, the chain being as the case may be substituted with one or more hydroxyl or amino groups, one or more trifluoromethyl groups, —COM, —COOM, or —CH$_2$COOM group (where M represents a hydrogen atom or a C1 to C18 alkyl group with a straight or branched chain substituted as the case may be with one or more hydroxyl and/or amino groups), a nitroso or a cyano group;

R$^5$ represents a hydrogen atom or a C1 to C5 alkyl group

R$^{12}$ represents a hydrogen atom or a —C—CO$_2$—(CH$_3$)$_3$ group, and the physiologically acceptable salts of these derivatives.

In certain aspects, the methods of the present disclosure include administering to a subject in need thereof a therapeutically effective amount of a paullone derivative represented by the compounds of Formula I and their pharmaceutically acceptable salts. In yet other aspects, the present disclosure provides for the production of medicaments for the treatment of mucoviscidosis (e.g., cystic fibrosis) or other diseases linked to a protein addressing error in cells, where the medicament comprises a paullone derivative represented by Formula I and its pharmaceutically acceptable salts.

In certain aspects, the methods of the present disclosure include treating mucoviscidosis and/or diseases linked to a protein addressing error in cells, by administering to a subject in need thereof a therapeutically effective amount of a family of paullone derivatives represented by general Formula (II), where Y represents a phenyl residue, together with the adjacent ring, and Z=C.

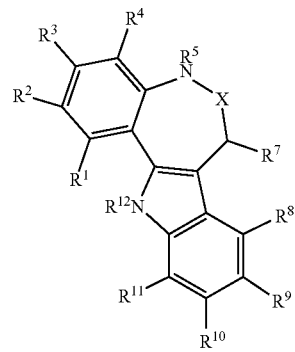
(II)

Where

X, R$^5$ and R$^{12}$ are as defined above, and

R$^5$ to R$^4$, R$^7$ to R$^{11}$, identical or different, represent an atom of hydrogen, halogen (F, Cl, Br, I), a hydroxyl, alkylenehydroxyl, alkynalkylenehydroxyl, alkynhydroxycyclohexyl, alkyl, alkoxy, alkylenealkoxy, alkylenecyano group, these radicals having C1 to C18 straight or branched chains, the alkylene group being saturated or unsaturated; the said chain being as the case may be substituted with one or more hydroxyl or amino groups, a trifluoromethyl group, a —COM, —COOM or —CH$_2$COOM group (where M represents a hydrogen atom, a C1 to C18 alkyl group with a straight or branched chain, substituted as the case may be with one or more hydroxyl and/or amino groups), a nitroso group or a cyano group; and the physiologically acceptable salts of such derivatives.

In yet other aspects, the methods of the present disclosure include treating mucoviscidosis and/or diseases linked to a protein addressing error in cells, by administering to a subject in need thereof a therapeutically effective amount of another family of paullones derivatives, where Y represents a thienyl residue, together with the adjacent ring, and Z=C. This family is represented by general Formula (III):

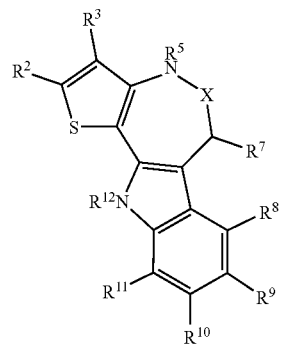
(III)

where the substituted groups have the meaning as in Formula (II).

Yet other suitable pallulone derivatives for treating mucoviscidosis and/or diseases linked to a protein addressing error in cells, comprises Y as a phenyl group together with the adjacent ring and Z=N. These compounds are represented by formula (IV):

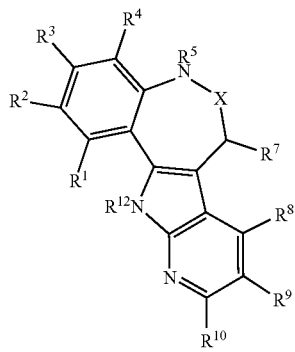

(IV)

where the substituted groups have the meaning given above with respect to Formula (II). In certain paullone derivatives of these various families, X optionally represents C=O.

In certain aspects, the methods of the present disclosure include treating mucoviscidosis and/or diseases linked to a protein addressing error in cells, by administering to a subject in need thereof a therapeutically effective amount of kenpaullone, which is represented by Formula V and its pharmaceutically acceptable salts.

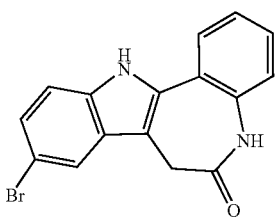

(V)

In yet other aspects, the present disclosure provides for the production of medicaments for the treatment of mucoviscidosis (e.g., cystic fibrosis) and diseases linked to a protein addressing error in cells, where the medicament comprises kenpaullone represented by the formula (V) and its pharmaceutically acceptable salts.

When developing the various active ingredients or medicaments according to the present disclosure, the active principles used in therapeutically efficient quantities are mixed with pharmaceutically acceptable vehicles for the administration route chosen. Thus, for oral administration, medicaments are optionally prepared in the form of gelatine capsules, tablets, SC tablets, capsules, pills, drops, syrups and the like. Such medicaments may contain 1 to 100 mg of active principle per unit. For parenteral administration (intravenous, subcutaneous, intramuscular injection), the medicaments are presented in the form of sterile or sterilisable solutions. They may also be in the form of suspensions or emulsions. In certain aspects, the medicaments of the invention are more particularly administered in the form of aerosols.

Doses per administration unit may vary from 1 to 50 mg of active principle or ingredient. The daily posology (e.g., dosage) is chosen so as to obtain a final concentration not exceeding 100 μM of the paullone derivative compounds of the present teachings in the blood of patients undergoing treatment. Other characteristics and advantages of the invention will be described in the experimental section herein by way of further non-limiting illustration.

Materials and Methods

M1. Cell Culture

CHO-WT cells: CHO (Chinese Hamster Ovary) cells are fibroblasts transfected with the wild-type CFTR gene (CFTR-WT). These cells will therefore overexpress the CFTR protein.

Culture medium: MEM alpha medium (GIBCO)+7% fetal calf serum+0.5% penicilline/streptomycin+100 μM methotrexate (amethopterine, Sigma).

CF15 cells: CF15 cells are human nasal epithelial cells expressing the ΔF508-CFTR gene.

Culture medium: DMEM medium+HAM F12+10% FCS+0.6% penicillin/streptomycin+growth factors (5 μg/ml insulin, 5 μg/ml transferrin, 5.5 μM epinephrine, 0.18 mM adenine, 10 ng/ml EGF, 2 nM T3, 1.1 μM hydrocortisone).

Calu-3 cells: Calu-3 cells are human lung epithelial cells expressing the wild-type CFTR gene.

Culture medium: DMEM/F12 medium with glutamax+7% fetal calf serum+1% penicillin/streptomycin.

M2. Immunolabelling

Immunolabelling allows visualising the cellular localisation of the CFTR protein by an anti-CFTR primary antibody (Ab), and a secondary Cy3-labelled fluorescent antibody directed against the primary antibody.

The cells are first seeded on cover slips in an appropriate culture medium. The cells are then washed 3 times with TBS (157 mM NaCl, 20 μM Tris base, pH 7.4) of 5 min. each time and then fixed by adding 3% TBS-paraformaldehyde for 20 min. After 3 washes with TBS (5 min), the cells are incubated with 0.1% TBS-triton (10 min) to make holes in the cell membrane, and then washed 3 times with TBS before being exposed to 0.5% TBS-BSA-0.05% saponin for 1 hr. The cells are then incubated with the primary anti-CFTR C terminal antibody (2 μg/ml) for 1 hr. The cells are washed 3 times (5 min. each) with TBS-BSA-saponin before incubating with the GAM-cy3 secondary antibody (1/400) for 1 hr. After 2 TBS washes (5 min. each), the nuclei are labelled by incubating with Topro3 (1/1,000) for 5 min. Finally, the cover slips can be mounted on a glass slide after 3 final TBS washes of 5 min. each. The slides are observed with a confocal microscope (Bio-Rad) using laser excitation at appropriate wave-lengths. In order to differentiate Cy3 from Topro3 labelling, the colour of the Topor3 fluorescence has been changed to blue (colour of the nuclei).

M3. Efflux of Radiotracers

Measurements of chloride ion transport in the cells were performed using the radioactive iodide efflux technique (Becq et al., Journal of Biological Chemistry 274, 27415-27425 (1999); Dormer et al., Journal of Cell Science 114, 4073-4081 (2001). The $^{125}I$ tracer is incorporated into the intracellular milieu. Then, the quantity of radiotracer coming out of the cell is then measured after adding various pharmacological agents. Iodide is used as a tracer of chloride ion transport. $^{125}I$ has the advantage of being short-lived compared to other markers such as $^{35}Cl$ (respective half-lives: 30 days and 300,000 years).

The cells are incubated in an appropriate medium in 24-well plates. The cells are rinsed twice with efflux medium (136.6 mM NaCl, 5.4 mM KCl, 0.3 mM $KH_2PO_4$, 0.3 mM $NaH_2PO_4$, 4.2 mM $NaHCO_3$, 1.3 mM $CaCl_2$, 0.5 mM $MgCl_2$, 0.4 mM $MgSO_4$, 10 mM HEPES, 5.6 mM D-glucose) in order to eliminate dead cells, which release radioactivity in an anarchic fashion. Then, the cells are then incubated with a 500-μl load (1 μCi/ml $^{125}INa$) for 30 min for CHO-WT or 1 hr for CF15 and Calu-3 cells. The iodide equilibrates on either side of the cell membrane. The following steps are performed using a robot (MultiPROBE, Packard): the loading medium is rinsed with efflux medium in order to eliminate extracellular radioactivity. The supernatant is collected every minute into haemolysis tubes and the medium is replaced by an equivalent volume of medium (500 µl). No drug is added to the samples taken in the first three minutes in order to obtain a stable baseline characterising the passive exit of I ions. The 7 samples that follow are obtained in the presence of the molecule to be tested. At the end of the experiment, the cells are lysed by adding 500 µl of 0.1 N NaOH/0.1% SDS (30 min), which allows determining the level of radioactivity remaining inside the cell. The radioactivity present in the haemolysis tubes is measured as counts per minute (cpm) using a gamma counter (Cobra II, Packard). The results in cpm are expressed as velocity of radioactive iodide efflux (R) according to the formula: $R (min^{-1})=[\ln(^{125}I\ t_1)-\ln(^{125}I\ t_2)]/(t_1-t_2)$ where $^{125}I\ t_1$=cpm at time $t_1$ and $^{125}I\ t_2$=cpm at time $t_2$. This iodide flux is represented by a graph. In order to quantify the iodide efflux due to administration of the tested molecule, the relative flux is calculated as follows in order to ignore the basal flux: Relative velocity $(min^{-1})$=Rpeak−Rbasal. Finally, these results are normalised in order to compare the effect of one drug versus another. The results are presented in the form of a mean+/−SEM. Student's statistical test is used to compare the effect of the various drugs with the controls (the corresponding P<0.01 values are considered to be statistically significant).

M4. Cytotoxicity Test

The MTT cytotoxicity test is a calorimetric test based on the capacity of mitochondrial dehydrogenases to metabolise MTT (a yellow tetrazolium salt) into formazan (purple). The absorbance is proportional to the concentration of converted dye and can then be measured by spectrophotometry. The cells are incubated in 96-well microplates in the presence of the agent to be tested for 2 hours. Three controls are performed: 100% live cells: cells without any agent; 0% live cells: cells left under normal atmosphere; blank: medium without cells. The cells are rinsed with RPMI medium without phenol red in order for the colour of the medium not to interfere with absorbance measurements. They are then incubated for 4 hours with 100 µl RPMI solution supplemented with MTT (0.5 mg/ml). The medium is eliminated, 100 µl DMSO is added which permit to dissolve the converted dye (formazan). The absorbance is measured by spectrophotometry at 570 nm (purple); 630 nm (background noise). In order to ignore the background noise, the following calculation is performed: $DO_{reelle}=DO_{570nm}-DO_{630nm}$. The results are then normalised with respect to the controls (100% and 0% live cells) and presented in the form of a mean+/−SEM.

Results

R1. Effect of Kenpaullone on delF508 Addressing in CF15 Cells.

The study of delF508-CFTR protein addressing is performed in the laboratory by using a combination of pharmacological, cellular imagery, biochemical and electrophysiological tests on CF15 human lung epithelial cells homozygous for the delF508 deletion. For each experiment, the addition of a cocktail (10 µM Forskoline+30 µM Genisteine) allows activation of the CFTR when the latter is localised at the membrane. This allows an iodide efflux to be observed if delF508 addressing has been restored. The results, presented in the form of a histogram, were normalised with respect to a standard treatment (treatment of the cells with 250 µM MPB-91 for 2 hrs), considered to represent 100% CFTR activity. FIG. 1 shows that a 2 hrs treatment with kenpaullone restores delF508-CFTR activity to a level that is higher than that obtained with MPB-91. However, alsterpaullone (100 µM) under the same experimental conditions as with kenpaullone has no effect (FIG. 1). These results show that treatment of CF15 cells for 2 hrs at 37° C. with kenpaullone, but not with alsterpaullone, restores addressing of the delF508 protein and allows it to function as an ion transporter (FIG. 1).

Figure 2:
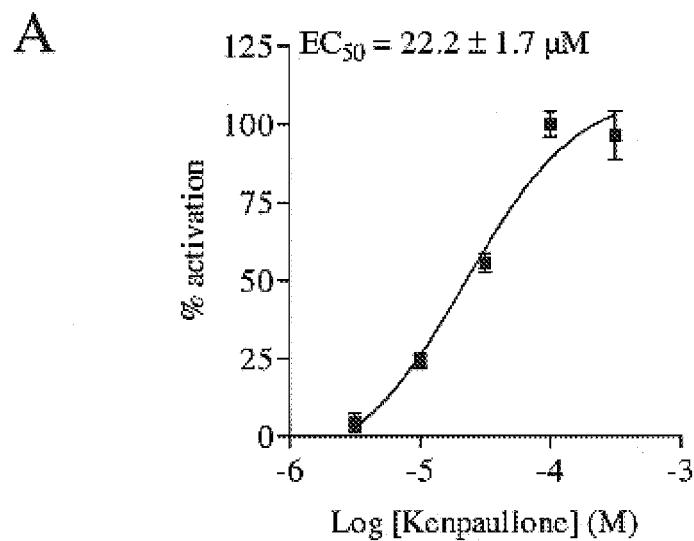
FIG. 2A: percentage of CFTR activation as a function of the log between [kenpaullone] (M) and the FIG. 2B: the effect of known CFTR inhibitors on delF508 activity after treatment with kenpaullone.
Figure 2:
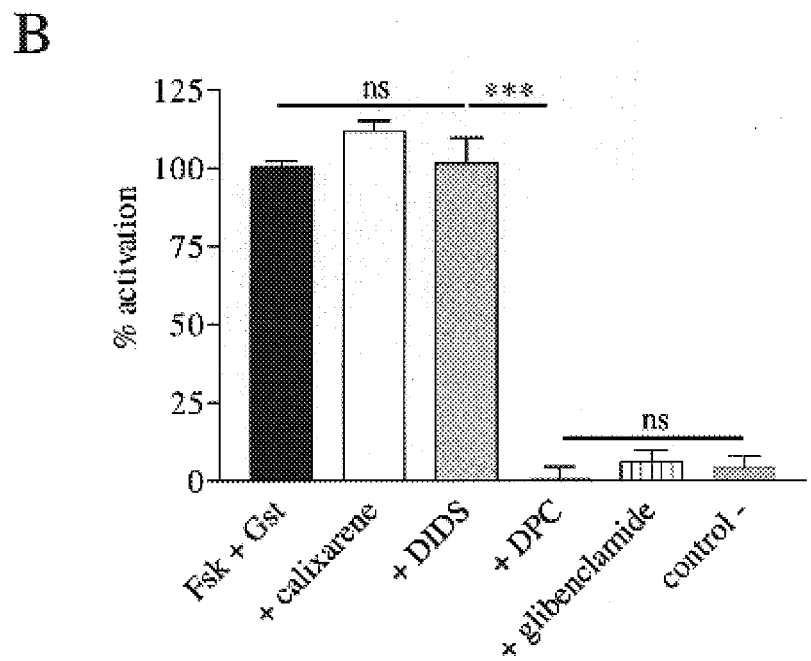

Without cells treatment, the delF508 protein is not membranous and no iodide efflux is observed as a result of stimulation with the cocktail (10 µM Forskoline+30 µM Genisteine). The $Ec_{50}$ (molecular concentration giving 50% of maximal efficiency) for kenpaullone was found to be 22±1.7 µM, (FIG. 2A, n=4 in each case). In order to characterise the effect observed, the effect of known CFTR inhibitors on delF508 activity was tested after treatment with kenpaullone. The results presented in FIG. 2B show that this transport is blocked by glibenclamide and DPC but insensitive to DIDS and calixarene. This pharmacological profile corresponds to that of CFTR.

Figure 3:
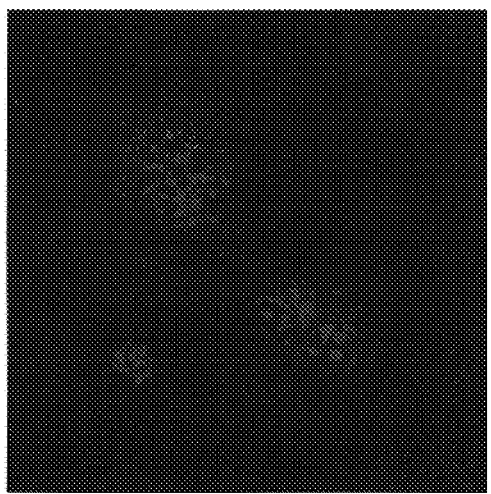
FIG. 3A: a photograph showing the localisation of delF508 in intra-cellular compartments.
FIG. 3B: a photograph showing the re-direction of the protein towards the membrane, after treatment with the kenpaullone.
Figure 3:
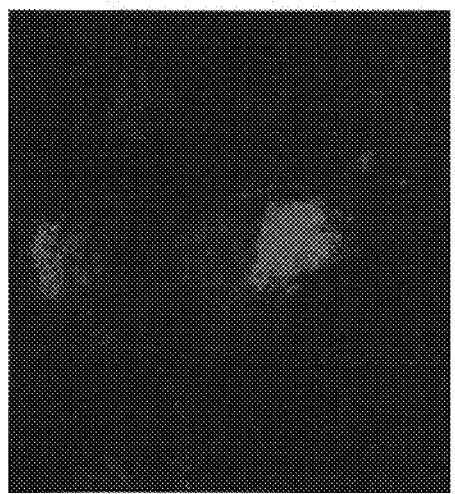
Figure 3:
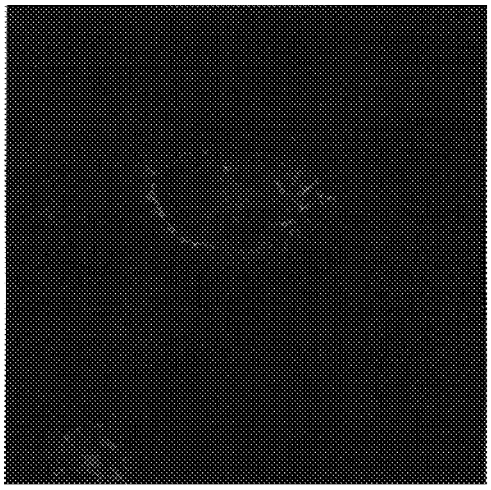
Figure 3:
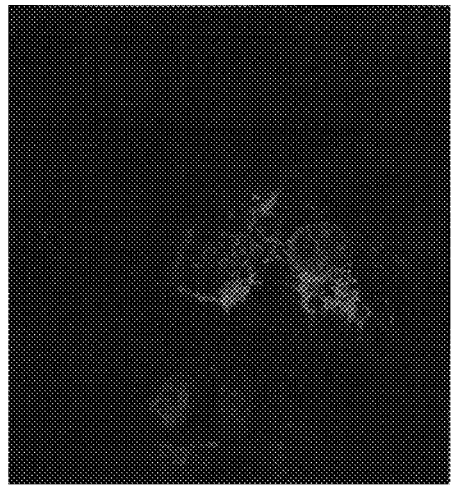

In CF patients, the delF508 protein is not present in the plasma membrane, because of the addressing errors in the protein which remains in the endoplasmic reticulum (ER). Cellular imagery of CF15 cells showed that the delF508 protein was localised in intracellular compartments (FIG. 3A). In contrast, treatment with 100 µM kenpaullone makes it possible to redirect the delF508 protein towards the membrane, as shown in FIG. 3B.

Figure 4:
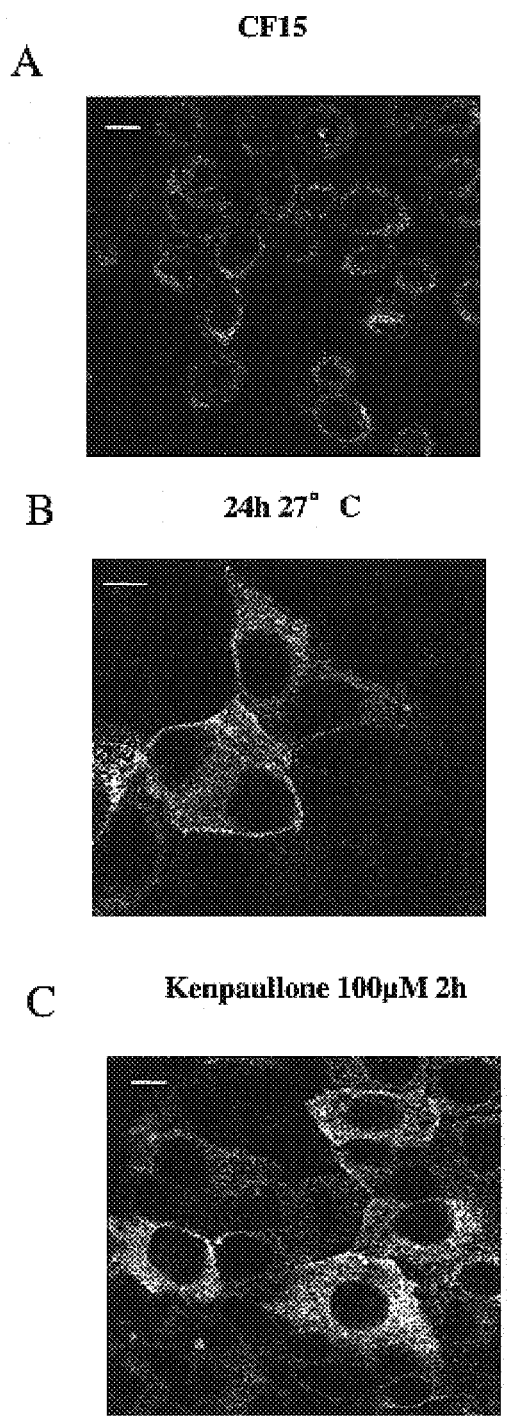
FIGS. 4A to 4C: the immunolocalisation of delF508-CFTR, after a 2 hrs treatment or in the absence of treatment.

FIGS. 4A to 4C also illustrate the immunolocalisation of delF508-CFTR after 2 hrs of treatment with kenpaullone or in the absence of treatment. This involves confocal visualisation of CFTR-delF508 in CF15 cells using a mouse anti-CFTR monoclonal antibody. CF15 cells treated for 24 hrs at 27° C. were used as a positive control.

Figure 5:
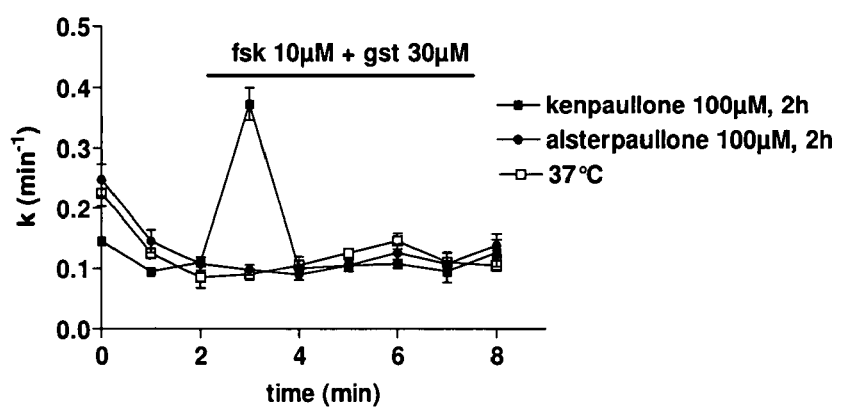
FIGS. 5A and 5B: activation of delF508-CFTR in CF15 cells after treatment with kenpaullone.
Figure 5:
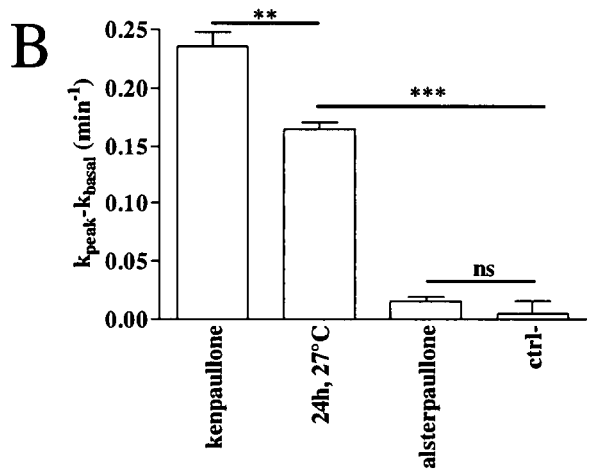

FIGS. 5A and 5B represent the activation of delF508-CFTR in CF15 cells after treatment with kenpaullone and, for comparison, with alsterpaullone. The iodide efflux was observed after 2 hrs of incubation with 100 µM of the tested compound or in the absence of treatment. CF15 cells treated for 24 hrs at 27° C. were used as a positive control and untreated CF15 cells as a negative control (37° C.).

The table below summarises the kenpaullone and ER chaperon machinery competition experiments performed by the iodide efflux technique.

| | BFA 20 µM | Tunicamycine 10 µM | Swainsonine 100 µM | Castanopermine 100 µg/l | Thapsigargine 10 µM | MG132 20 µM | Geldanamycine 2.5 µg/ml |
|---|---|---|---|---|---|---|---|
| Potentiation of the kenpaullone effect | — | ** | ** | * | * | ns | ns |
| | | Inhibitors of glycosylation | | Inhibitors of calnexin | | Degradation pathway of inhibitors | |

— inhibition, ** P < 0.01, * P < 0.1, ns P > 0.1 (Student's t-test)

Inhibition of kenpaullone by Brefeldine A (BFA), an inhibitor of the ERGIC vesicular transport, is observed, which shows that kenpaullone induces the readdressing of the delF508-CFTR protein. No modulation of the effect of kenpaullone is observed in the presence of MG132, a proteasome inhibitor, which shows there is competition between kenpaullone and MG132.

R2. Effect of Kenpaullone on CFTR Activity in Calu-3 Cells

In order to show that the effect of kenpaullone is specific for delF508 addressing and does not alter other chloride ion channels, kenpaullone was tested as a potential activator in Calu-3 cells. These results were obtained using the iodide efflux technique. Our controls are the forskoline (5 µM, n=8) and the MPB-91 (250 µM, n=8), the Kenpaullone (n=8) was not found to be an activator of wild-type CFTR or any other anionic transporter in these cells (no significant difference).

R3. Effect of Kenpaullone on CFTR Addressing in Calu-3 Cells

In order to show that the effect of kenpaullone is specific to delF508 addressing, kenpaullone was tested as a modulator of wild-type CFTR addressing in Calu-3 cells. These results were obtained by measuring iodide efflux in Calu-3 cells treated for 2 hrs with kenpaullone (100 µM). The CFTR activity under such experimental conditions is not significantly different from the controls. These results demonstrate that kenpaullone does not affect the addressing pathway of the wild-type CFTR or other chloride ion channels, nor does it alter CFTR activity in non-CF human lung epithelial cells.

R4. Cytotoxicity of Kenpaullone

In order to test the cytotoxicity of kenpaullone, CHO-WT cells were incubated for 2 hrs with different concentrations of inhibitors before being tested for viability with MTT. The results show that the cells are viable at all concentrations of kenpaullone. Therefore, this molecule does not present any cell cytotoxicity.

Efflux tests revealed that kenpaullone allows the membranous relocation of the delF508-CFTR protein, thus restoring its transmembrane transport capacity, inhibits the degradation pathway and seems to modulate the interaction between CFTR and calnexine (calcium-treatment dependent mechanism). Treatment of CF cells with kenpaullone thus appears to interfere with the capacity of the control machinery to interact and retain the protein in the endoplasmic reticulum through inhibition of calnexine and chaperon molecules that intervene in the degradation pathway. This molecule is not toxic in the tests that were used. Furthermore, kenpaullone toxicity studies in animals have shown only very slight toxicity. A high plasma concentration can be attained by coupling with PEG. Kenpaullone is considered to be highly selective for GSK-3 inhibition.

Example

An inhalation solution is prepared with an ampoule rebulizer starting with sodium chloride, dehydrated calcium chloride and water for injectable preparations. The kenpaullone is added as active ingredient. The solution is formulated in 2.5 ml ampoules. Ampoules containing 5, 10 mg or 20 mg of kenpaullone can be prepared in this way.

The invention claimed is:

1. A method of treating mucoviscidosis in a subject, the method comprising administering to the subject in need thereof a therapeutically effective amount of a paullone derivative represented by the formula (I):

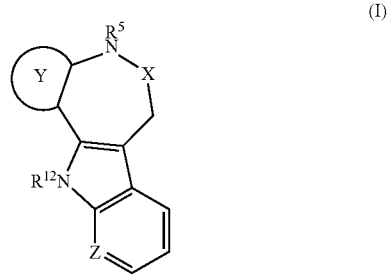

Wherein
- —X represents a C=O, C—S—CH$_3$, C—S or —C—NHOH group;
- Z represents C or N;
- Y represents a phenyl or a thienyl residue, together with the adjacent ring;

the ring(s) that constitute such derivatives being substituted as the case may be with one or more halogen atoms, hydroxyl, alkylenehydroxyl, alkynalkylenehydroxyl, alkynhydroxycyclohexyl, alkyl, alkoxyl, alkylenealkoxyl, alkylenecyano groups, the alkylene group being saturated or unsaturated, such C1 to C18 radicals having a straight or branched chain, said chain may be substituted with one or more hydroxyl or amino groups, one or more trifluoromethyl groups, —COM, —COOM, or —CH$_2$COOM group (where M represents a hydrogen atom or a C1 to C18 alkyl group with a straight or branched chain substituted as the case may be with one or more hydroxyl and/or amino groups), a nitroso or a cyano group;

$R^5$ represents a hydrogen atom or a C1 to C5 alkyl group $R^{12}$ represents a hydrogen atom or a —C—CO$_2$—(CH$_3$)$_3$ group, and the physiologically acceptable salts of these derivatives.

2. The method according to claim 1, wherein Y represents a phenyl residue, together with the adjacent ring, and Z=C, the corresponding family being represented by general formula (II):

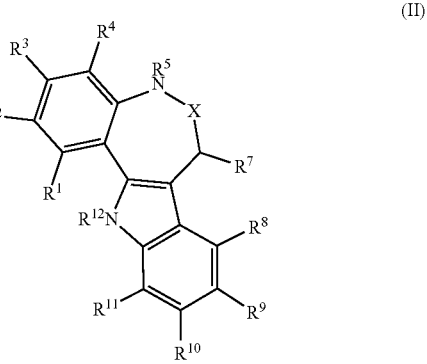

Wherein
X, $R^5$ and $R^{12}$ are as defined supra, and
$R^1$ to $R^4$, $R^7$ to $R^{11}$, identical or different, represent an atom of hydrogen, halogen (F, Cl, Br, I), a hydroxyl, alkylenehydroxyl, alkynalkylenehydroxyl, alkynhydroxycyclohexyl, alkyl, alkoxy, alkylenealkoxy, alkylenecyano group, these radicals having C1 to C18 straight or branched chains, the alkylene group being saturated or unsaturated; said chain may be substituted with one or more hydroxyl or amino groups, a trifluoromethyl group, a —COM, —COOM or —CH$_2$COOM group (where M represents a hydrogen atom, a C1 to C18 alkyl group with a straight or branched chain, substituted as the case may be with one or more hydroxyl and/or amino groups), a nitroso group or a cyano group; and the physiologically acceptable salts of such derivatives.

3. The method according to claim 1, wherein Y represents a thienyl residue, together with the adjacent ring, and Z=C, the corresponding family being represented by general formula (III):

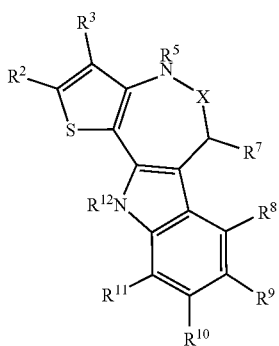

(III)

wherein the substituted groups have the meaning given in claim 2 with respect to formula (II).

4. The method according to claim 1, wherein Y forms a phenyl group together with the adjacent ring and Z=N, the corresponding family being represented by formula (IV):

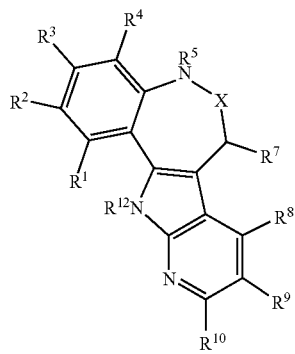

(IV)

wherein the substituted groups have the meaning given in claim 2 with respect to formula (II).

5. The method according to claim 1, wherein X represents C=O.

6. A method of treating mucoviscidosis in a subject, the method comprising administering to the subject in need thereof a therapeutically effective amount of kenpaullone represented by the formula (V):

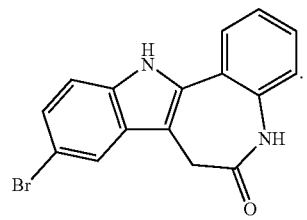

(V)

7. The method according to claim 6, wherein the kenpaullone is administered in a medicament in the form of gelatine capsules, tablets, SC tablets or capsules.

8. The method according to claim 6, wherein the kenpaullone is administered in a medicament prepared for parenteral administration, in the form of a solution.

9. The method according to claim 6, wherein the kenpaullone is administered in a medicament prepared for administration in the form of an aerosol.

10. The method according to claim 1, wherein said therapeutically effective amount results in a final concentration of less than or equal to about 100 µM in the blood of the subject being treated.

11. The method according to claim 1, wherein said therapeutically effective amount is about 1 mg to about 100 mg.

12. The method according to claim 1, wherein said therapeutically effective amount is about 1 mg to about 50 mg.

13. The method according to claim 6, wherein said therapeutically effective amount of kenpaullone results in a final concentration of less than or equal to about 100 µM of kenpaullone in the blood of the subject being treated.

14. The method according to claim 6, wherein said therapeutically effective amount of kenpaullone is about 1 mg to about 100 mg.

15. The method according to claim 6, wherein said therapeutically effective amount of kenpaullone is about 1 mg to about 50 mg.

* * * * *